(12) United States Patent
Linnane et al.

(10) Patent No.: US 7,723,559 B2
(45) Date of Patent: May 25, 2010

(54) WOUND DRESSING

(75) Inventors: Patrick G. Linnane, Chester (GB); Helen L. Shaw, Widnes (GB)

(73) Assignee: ConvaTec Technologies Inc., Reno, NV (US)

( * ) Notice: Subject to any disclaimer, the term of this patent is extended or adjusted under 35 U.S.C. 154(b) by 1383 days.

(21) Appl. No.: 10/820,270

(22) Filed: Apr. 8, 2004

(65) Prior Publication Data

US 2004/0249328 A1 Dec. 9, 2004

(30) Foreign Application Priority Data

Apr. 10, 2003 (GB) ................... 0308311.0

(51) Int. Cl.
*A61F 13/00* (2006.01)
(52) U.S. Cl. .......................... 602/42; 602/56
(58) Field of Classification Search ............ 602/41–43, 602/47–48, 56, 59; 128/888, 889; 606/213, 606/215
See application file for complete search history.

(56) References Cited

U.S. PATENT DOCUMENTS

| 4,029,103 | A | * | 6/1977 | McConnell | ............... 604/179 |
| 4,915,694 | A | | 4/1990 | Yamamoto et al. | |
| 5,197,945 | A | | 3/1993 | Cole et al. | |
| 5,447,492 | A | * | 9/1995 | Cartmell et al. | ............... 602/58 |
| 5,554,106 | A | | 9/1996 | Layman-Spillar et al. | |
| 6,482,192 | B2 | | 11/2002 | Haarer et al. | |
| 6,552,244 | B1 | * | 4/2003 | Jacques et al. | ............... 602/43 |
| 6,566,575 | B1 | * | 5/2003 | Stickels et al. | ............... 602/41 |
| 6,700,034 | B1 | * | 3/2004 | Lindsay et al. | ............... 604/378 |

FOREIGN PATENT DOCUMENTS

| DE | 29923683 | | 1/2001 |
| EP | 0076896 | | 6/1985 |
| EP | 0691113 A1 | * | 5/1995 |
| EP | 0659390 | | 6/1995 |
| EP | 0659390 A3 | | 6/1995 |
| EP | 0691113 | | 1/1996 |
| GB | 2211417 | | 7/1989 |
| GB | 2290031 A | | 12/1995 |
| WO | WO 93/00788 A2 | | 1/1993 |
| WO | WO 94/16746 | | 8/1994 |
| WO | WO 00/01425 | | 1/2000 |

* cited by examiner

*Primary Examiner*—Michael A. Brown
(74) *Attorney, Agent, or Firm*—John M. Kilcoyne

(57) ABSTRACT

A wound dressing for post-operative sites requiring drainage includes a thin film or film/foam laminate layer with an adhesive applied to one surface thereof and an absorbent layer positioned on the adhesive surface. The dressing has an aperture to accommodate a drainage tube and a slit extending from the aperture to an outer edge of the dressing.

20 Claims, 2 Drawing Sheets

WOUND DRESSING

Figure 1:
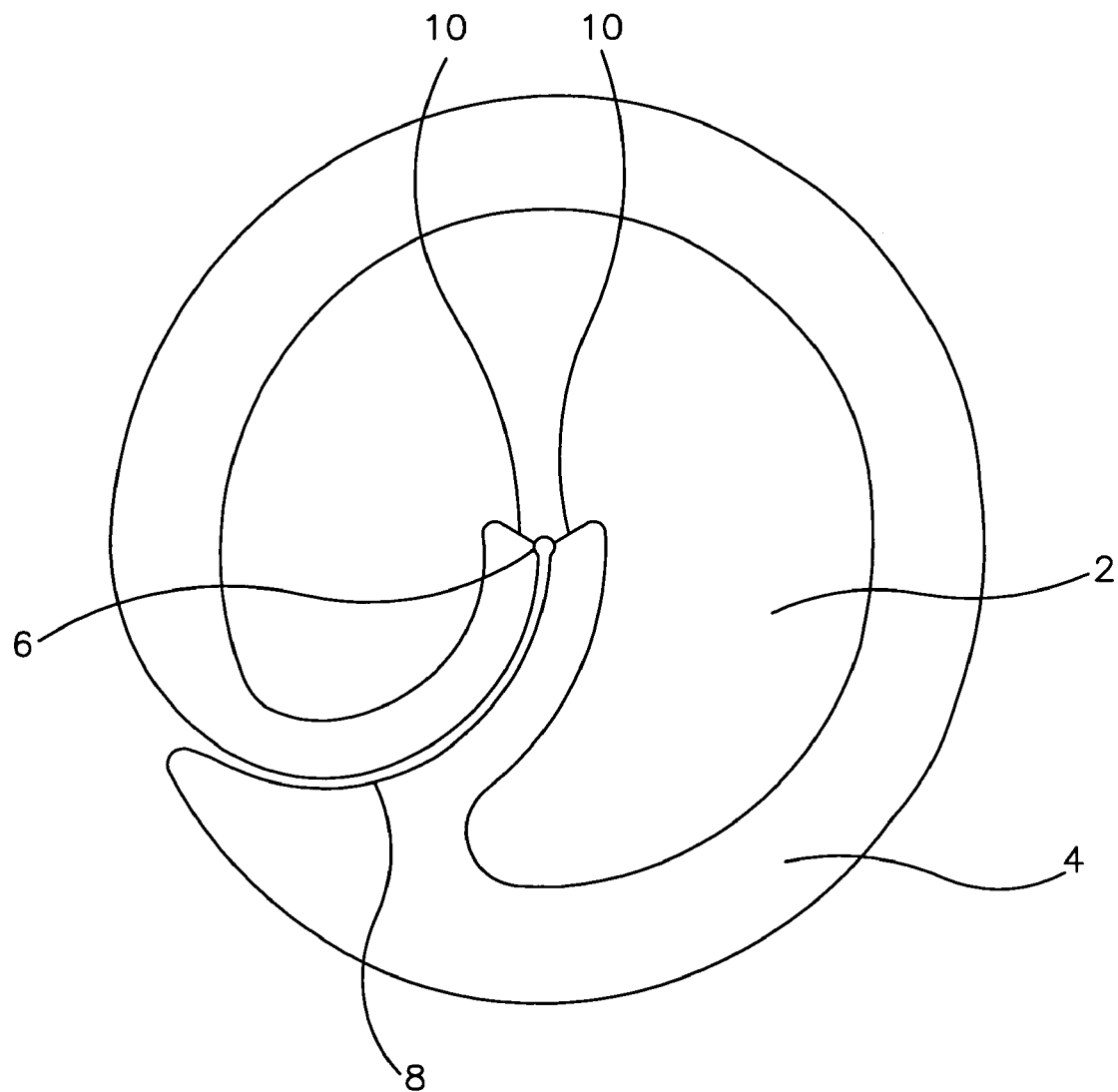

This application claims the benefit of priority of United Kingdom Patent Application No. 0308311.0, filed Apr. 10, 2003.

The present invention relates to a wound dressing particularly, but not exclusively, for use as a dressing on post-operative wounds that require a drain to remove wound fluid.

For wounds producing some exudate, post-operative wound dressings may be of the type which comprise a thin polymeric film and a low adherency absorbent pad. Such a dressing is sold under the name OpSite Post-Op™ by Smith and Nephew. A disadvantage of such dressings is that if the wound requires drainage via a drainage tube the dressing has to be cut by nursing staff so that the drainage tube can be accommodated.

The absorbent pad also reduces greatly the flexibility of the dressing meaning that a post-operative dressing with an absorbent pad may be difficult to apply to certain areas of the body and particularly around a drainage site and may be uncomfortable to wear. Cutting the dressing to accommodate the drainage tube can release loose fibres from the absorbent pad, which could be lost into the wound, and is a time consuming inconvenience for health care staff.

A further disadvantage is that if it is necessary to cut the dressing, it is not possible to make a complete seal around the incision made for the drain and therefore there is a higher risk of infection. There may also be a higher risk of leakage because the dressings are generally cut to remove a long narrow oblong of dressing, wider than the drain tube, which leaves a corresponding area of the site uncovered. Any wound fluid entering this area will not be absorbed.

There is thus a need for a wound dressing suitable for use on post-operative wounds which is capable of absorbing wound fluid at the rate generally produced by such wounds but which accommodates a drainage tube without the need to cut the dressing.

We have now invented a wound dressing for post-operative sites which alleviates the above problems by combining absorption and the capability to accommodate a drainage tube, the dressing being in a conformable format and there is provided by a first embodiment of the present invention a wound dressing for post-operative sites requiring drainage comprising:

a thin film or film/foam laminate layer with an adhesive applied to one surface thereof;

an absorbent layer positioned on the adhesive surface of the thin film layer, the dressing being provided with an aperture to accommodate a drainage tube; and the dressing being slit from the aperture to an outer edge of the dressing.

We have found that wound dressings according to the invention may mitigate the problems associated with applying a dressing to a post-operative site that has a drainage tube. It is thought that this is in part achieved by the aperture and slit in the dressing which aids application of the dressing to the patient by it being possible to position the aperture around the drainage tube and then out and around the drain until the whole dressing is in place.

The thin film or film/foam laminate layer provides a viral and bacterial barrier to the wound. It is preferably made from polyurethane, has a thickness of 0.02 mm to 0.04 mm and is transparent. Preferably the thin film or film/foam laminate layer has a high MVTR. This allows moisture to evaporate from the dressing. The film or film/foam laminate layer preferably has an MVTR of at least 1500 gsm/24 hrs as measured by the method described in BP 1993 Appendix XX J1 or in the range of from 1000 gsm/24 hrs to 10000 gsm/24 hrs, preferably 1500 gsm/24 hrs to 5000 gsm/24 hrs.

Materials that may be used as the film include polyurethanes; polyureas; homo- and copolymers of vinyl acetate; polyethers; polymers comprising amide blocks; homo- and copolyesters; or a combination of two or more of these. A film/foam laminate may be an expanded polyurethane foam laminated to a polyurethane film.

An absorbent layer is preferably present to absorb exudate from the wound. The layer preferably has an absorbency of at least 10 g of sodium chloride and calcium chloride solution (BP 1995 Appendix 1A) per gram of absorbent layer as measured by the absorbency test for alginate dressings BP 1995. The absorbent layer may form the wound contact layer of the dressing. The absorbent layer preferably forms a transparent gel on contact with exudate which gel comes into intimate contact with the wound and helps to increase conformability and mobility at the wound site. The absorbent layer is preferably fibrous and most preferably comprises gel forming fibres.

The gel forming fibres are preferably chemically modified cellulosic fibres in the form of a fabric and in particular carboxymethylated cellulose fabrics as described in WO/00/01425 to Akzo Nobel UK Ltd or WO 94/16746 to Courtaulds PLC. The carboxymethylated cellulosic fabrics preferably have a degree of substitution of between 0.12 to 0.45 as measured by IR spectroscopy (as defined in WO/00/01425) and are made by carboxymethylating a woven or non-woven cellulosic fabric such that the absorbency is increased. Particularly preferred fabrics have an absorbency of between 15 g/g of sodium/calcium chloride as defined above to 30 g/g of sodium/calcium chloride as measured by the method defined above. Particularly preferred fabrics have an absorbency of 20 g/g to 30 g/g and most preferred of 25 g/g to 28 g/g of sodium/calcium chloride as measured by the method defined above.

The cellulosic fabric preferably consists solely of cellulosic fibre but may contain a proportion of non-cellulosic textile fibre or of gel-forming fibre. The cellulosic fibre is of known kind and may comprise continuous filament yarn and/or staple fibre. The carboxymethylation is generally performed by contacting the fabric with strong alkali and a carboxymethylating agent such as chloroacetic acid in an aqueous system.

Another suitable gel forming fibre comprises alginate fibre. Alginate fibres may be used alone in the absorbent layer or in admixture with non-cellulosic textile fibres, with other gel-forming fibre such as carboxymethyl cellulose fibre, or with both. A particularly preferred such fibre is an absorbent, composite fibre comprising a matrix of from at least 10% to less than 50% by weight of water insoluble alginate, such as calcium alginate, having dispersed therein at least 40% by weight of another polysaccharide. Suitably, the other polysaccharide may be selected from the group comprising carboxymethyl cellulose, carboxyethyl cellulose, other derivatives of cellulose, cellulose, pectin, hyaluronic acid and chitosan.

The fabric is preferably of a non-woven type to reduce fibre shedding in the wound.

The absorbent layer preferably has a low lateral wicking rate so that exudate is not spread across the full extent of the layer. This has the advantage of reducing maceration in the skin surrounding the wound.

Preferably the lateral wicking rate is from 10 mm per minute to 40 mm per minute. More preferably the lateral wicking rate is from 10 to 20 mm per minute.

The adhesive layer of the present invention is applied to the thin film or film/foam laminate layer and may adhere the dressing to the skin for instance where the absorbent layer is an island surrounded by the thin film or film/foam laminate. Preferably the adhesive composition comprises a homogeneous blend of one or more water soluble hydrocolloids and one or more low molecular weight polyisobutylenes such as are described in EP-B-92999 incorporated herein by reference. The water soluble hydrocolloids may be selected from sodium carboxymethylcellulose, pectin, gelatin, guar gum, locust bean gum, gum karaya and mixtures thereof. The polyisobutylenes may be selected from low molecular weight polyisobutylenes having a viscosity average molecular weight of from 36,000 to 58,000 Florey. The adhesive layer is capable of absorbing exudate while maintaining adhesion of the dressing to the skin.

Alternatively the adhesive composition may comprise a homogeneous blend of one or more hyrdocolloids, one or more low molecular weight polyisobutylenes one or more styrene block copolymers, mineral oil, butyl rubber, a tackifier and small amounts of optional components. By selection of specific ranges of the amounts of the above listed components, adhesive compositions may be prepared having good adhesion to the skin and stretchability. Such compositions and the preparation thereof are disclosed in EP-B-130061 incorporated herein by reference.

Alternatively the adhesive may be a polyamide web.

The dressing may also include a further adhesive layer overlying the absorbent layer. The further adhesive layer may form the wound contacting surface and may also allow the dressing to be adhered to the skin. This further adhesive layer may have a composition as described above and may also comprise reinforcing fibres such as described in EP-B-130061 and EP-A-621041 to aid in the maintenance of the structural integrity of the dressing. Preferably the reinforcing fibres are present at a level of from 2% to 10% by weight of the adhesive composition. The adhesive layer may be substantially free from apertures; alternatively, it may include a plurality, preferably as a regular array, of apertures from 0.25 to 10 mm in diameter, especially from 5 to 8 mm in diameter.

The further adhesive layer forming the wound contacting surface may be in the form of a layer of the island type where different regions of the adhesive layer have different properties, for example, the adhesive layer could comprise a central zone of swellable material backed and surrounded by a more rigid adhesive, or the adhesive layer could be apertured to allow rapid uptake of exudate into the dressing.

The dressing will typically be made in three sizes, all dressings preferably being about 0.6 mm thick. The dressing is preferably circular with a central aperture and curved full-thickness slit which extends from the aperture to the outside of the dressing. The curved slit may aid the application of the dressing to a wound with a drainage tube, and may make the sealing of the slit easier when the dressing is positioned on use on a wound.

In a second embodiment of the invention, the dressing is preferably elliptical with an aperture positioned towards one end of the long axis of the ellipse and with a curved slit extending from the aperture to an outside edge of the dressing.

Preferably the absorbent pad does not extend to the edges of the slit but is shaped so as to leave a border free of absorbent pad adjacent the slit. More preferably the dressing is provided with additional slits in the form of small cuts extending from the aperture for a short distance into the dressing in the immediate vicinity of the aperture but not extending to the outer edge of the dressing. The cuts are present to accommodate large drain tubes and enhance conformability of the dressing. There are preferably two cuts positioned at 120 degrees to the main slit.

The borders of the slit are preferably free of absorbent pad but are coated with adhesive so that the edges of the slit can be secured to the skin surrounding the wound or to a part of the dressing but also can serve to secure the drainage tube.

If, in use, the edges of the slit are not sealed, either by adherence to the skin or to another part of the dressing, then part of wound may be exposed thereby increasing the risk of infection. There may also be a higher risk of leakage of wound exudate.

Adhesive along the borders of the slit may allow both sides of the slit to be adhered to the skin to seal the slit in use. Alternatively, only one side (the first side) of the slit may be arranged to adhere to the skin, the other side (the second side) being arranged to overlap the first side to adhere to the outer surface of the dressing thereby sealing the slit in use.

In an alternative embodiment, in which a further adhesive layer overlies the absorbent layer to form the wound contacting surface, the absorbent pad may extend to the edge of the dressing, the further adhesive layer allowing the slit to be sealed in use.

Figure 2:
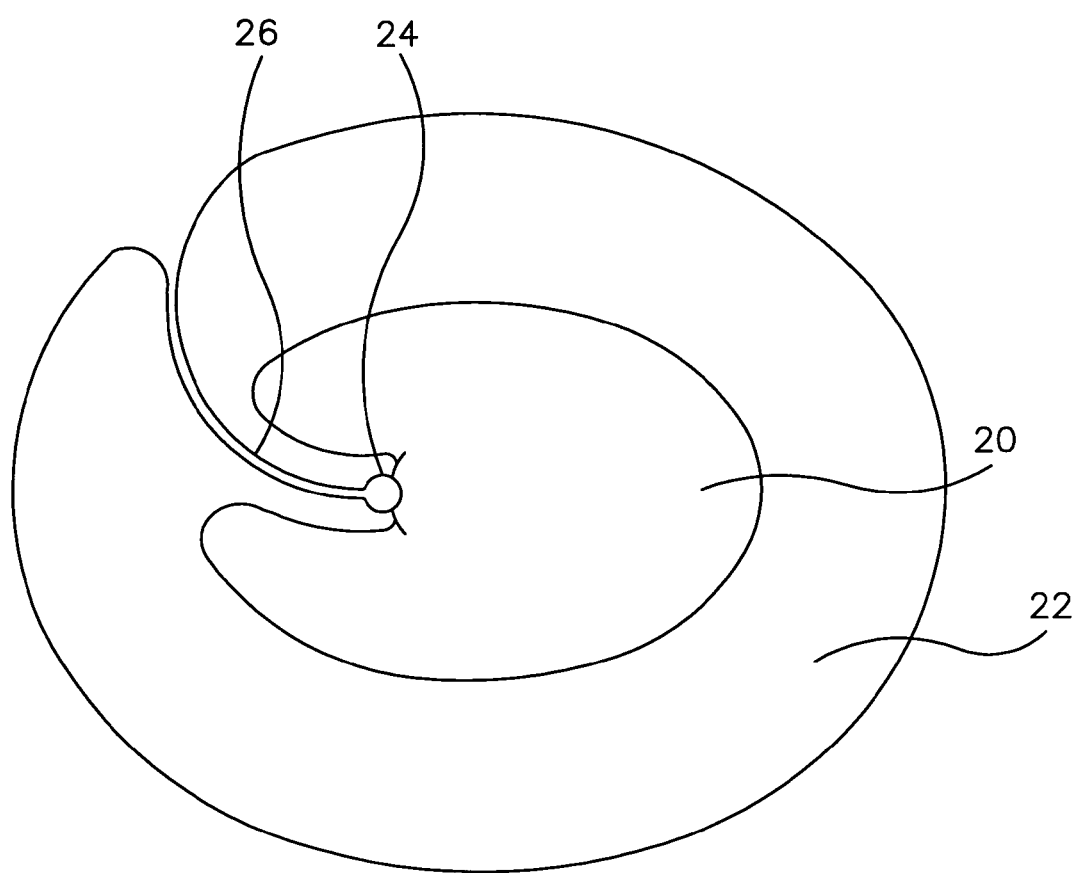

Preferred embodiments of the invention will now be illustrated in the following drawings in which:

FIG. 1 shows a plan view of a first embodiment of the skin-contacting surface of a wound dressing according to the invention; and FIG. 2 shows a plan view of a second embodiment of the skin-contacting surface of a wound dressing according to the invention.

With reference to the drawings and particularly FIG. 1 there is shown a first embodiment of a wound dressing according to the invention. The dressing comprises a central absorbent pad 2, surrounded by an adhesive border 4. The adhesive border 4 is in the form of a thin film which is coated with adhesive and to which the absorbent pad 2 is stuck. This creates a dressing with an island pad 2 surrounded by an adhesive border 4. The dressing is circular in shape to reduce rucking in use and has an aperture 6 at the centre which can accommodate a drain tube (not shown). The dressing has a full thickness slit 8 which extends from the aperture to the outside edge of the dressing. The pad 2 does not extend to the edges of the slit 8 so that adhesive borders are created along the edges of the slit 8. These assist in securing the drain tube.

The slit 8 is further provided with small cuts 10 in the immediate vicinity of the aperture 6 which allow the aperture to accommodate larger sized drainage tubes and enhance the conformability of the dressing.

The slit 8 is curved to aid the sealing of the dressing around the drain tube and reduce the risk of rucking. The curved slit also enhances conformability.

The dressing is applied by positioning the aperture around the drainage tube and then out and around the drain until the whole dressing is in place.

A second embodiment of the dressing is shown in FIG. 2. The dressing is of similar construction to that shown in FIG. 1 except that the dressing is elliptical in shape. The dressing has an absorbent pad 20 surrounded by an adhesive border 22. The dressing is provided with an aperture 24 and a full thickness slit 26 extending from the aperture to an outside edge of the dressing. The aperture is off-set towards one end of the long axis of the ellipse to allow the dressing to be applied closer to a primary surgical incision site than a dressing with a centrally located aperture could be. The elliptical shape of the dressing allows surgical drain sites to be dressed that are in close proximity to a primary surgical incision which is also dressed without the dressings overlapping in the area of skin between the two sites.

The wound dressing of the present invention may be made by obtaining an absorbent layer as described in WO 00/01425 and generally in Example 2 of that patent application having an absorbency of 25 g/g and a lateral wicking rate of 11 mm per minute in the form of a hydroentangled apertured fabric, press cut to the desired shape by a suitable die and bonding it to a polyurethane film coated with a hydrocolloid adhesive described above by conventional heat lamination/pressure techniques. Dressings can be press cut or roller cut from the laminated web.

An alternative wound dressing of the present invention, in which an additional adhesive layer is included on the wound facing side of the absorbent layer to form the wound contacting surface, can be made by obtaining an absorbent layer as described in WO 00/01425 having a low degree of substitution and in the form of a hydroentangled apertured fabric and bonding it to a polyurethane film coated with an adhesive by conventional heat lamination/pressure techniques. An adhesive is applied by extrusion in the correct dimensions onto silicone release paper and then transferred onto the absorbent layer of the dressing, either prior to or subsequent to the heat sealing process. In this way the adhesive is keyed into the absorbent layer via conventional pressure/heat lamination techniques to form an adhesive wound contacting surface. Dressings can be press cut or roller cut from the laminated web.

Alternatively a wound dressing according to the invention, with an adhesive wound contacting surface, can be made by placing an absorbent layer onto a flat surface and coating it with about 10 to 20 gms of a co-polyamide powder bond material. Then placing a polyurethane film material (plus its support) onto the co-polyamide powder bond layer and passing the assembly through a fusing press at about 100° C. A sheet of hydrocolloidal adhesive with 5 mm perforations is next placed onto the absorbent surface of the assembly and bonded (on the fusing press set at 80° C.). As explained above the adhesive is now keyed-in to the dressing forming an adhesive wound contacting layer. A fresh piece of release liner is placed across the hydrocolloid layer and the final dressings shape is cut out. The dressing may then be packaged and irradiated at 35.5 kGy.

The invention claimed is:

1. A wound dressing for post-operative sites requiring drainage comprising:
    a thin film or film/foam laminate layer with an adhesive applied to one surface thereof;
    an absorbent layer positioned on the adhesive surface of the thin film or film/foam laminate layer, the dressing being provided with an aperture to accommodate a drainage tube; and
    the dressing being slit, taking a curved path from the aperture to an outer edge of the dressing, and wherein the absorbent layer does not extend along an edge of the slit, leaving a border free of absorbent layer adjacent the slit.

2. The wound dressing as claimed in claim 1 wherein the dressing is circular in shape.

3. The wound dressing as claimed in claim 1 wherein the dressing is elliptical in shape.

4. The wound dressing as claimed in claim 1 wherein radial cuts extend from the aperture into the dressing but not to an outside edge of the dressing so that the aperture can accommodate large diameter drainage tubes.

5. The wound dressing as claimed in claim 1 wherein said absorbent layer becomes transparent on absorption of exudate.

6. The wound dressing as claimed in claim 1 wherein said absorbent layer is fibrous.

7. The wound dressing as claimed in claim 1 wherein said absorbent layer comprises gel forming fibres.

8. The wound dressing as claimed in claim 1 wherein said absorbent layer is a carboxymethylated fabric.

9. The wound dressing as claimed in claim 1 wherein said absorbent layer is a carboxymethylated cellulose fabric with a degree of substitution of cellulose groups measured by IR spectroscopy in the range of from 0.12 to 0.45.

10. The wound dressing as claimed in claim 1 wherein the dressing is made from Lyocell and has an absorbency of at least 10 g/g of sodium/calcium chloride solution.

11. The wound dressing as claimed in claim 1 wherein said absorbent layer comprises alginate fibres.

12. The wound dressing as claimed in claim 1 wherein said thin film layer or film/foam laminate is transparent.

13. The wound dressing as claimed in claim 1 wherein said thin film layer is a polyurethane film.

14. The wound dressing as claimed in claim 1 wherein said film/foam laminate is an expanded polyurethane foam laminated to a polyurethane film.

15. The wound dressing as claimed in claim 1 wherein said film or film/foam laminate layer extends beyond said absorbent layer for securing the dressing to the skin.

16. The wound dressing as claimed in claim 1 wherein the edge of the slit, which is free from the absorbent layer, is coated with an adhesive.

17. The wound dressing as claimed in claim 1 having a wound contacting surface wherein said absorbent layer is said wound contacting surface of the dressing.

18. The wound dressing as claimed in any of claim 1 wherein a further adhesive layer overlies said absorbent layer.

19. The wound dressing as claimed in claim 18 wherein said further adhesive layer is apertured.

20. The wound dressing as claimed in claim 18 having a wound contacting surface wherein said further adhesive layer is the wound contacting surface of the dressing.

* * * * *